United States Patent [19]

Biftu et al.

[11] Patent Number: 4,533,671

[45] Date of Patent: Aug. 6, 1985

[54] 5-(2,3-DIHYDRO-1H-PYRROLIZIN-5-OYL)-2-ALKANOIC OR CARBOXYLIC ACIDS AND ANALOGS AS ANTI-INFLAMMATORY AND ANALGESIC AGENTS

[75] Inventors: Tesfaye Biftu; Bruce E. Witzel; Peter L. Barker, all of Westfield, N.J.

[73] Assignee: Merck & Co., Inc., Rahway, N.J.

[21] Appl. No.: 433,603

[22] Filed: Oct. 8, 1982

[51] Int. Cl.$^3$ .................. C07D 207/26; A61K 31/40
[52] U.S. Cl. ..................... 514/413; 548/453
[58] Field of Search .......... 548/453; 424/274

[56] References Cited

U.S. PATENT DOCUMENTS

| | | | |
|---|---|---|---|
| 3,952,012 | 4/1976 | Carson | 548/527 |
| 4,048,191 | 9/1977 | Carson | 548/539 |
| 4,087,539 | 5/1978 | Muchowski | 514/443 |
| 4,097,579 | 6/1978 | Muchowski | 514/413 |
| 4,119,639 | 10/1978 | Carson | 548/527 |
| 4,232,038 | 11/1980 | Muchowski | 514/413 |

OTHER PUBLICATIONS

Carson & Wong, *J. Med. Chem.*, 16 (2), 172 (1973).

*Primary Examiner*—Richard L. Raymond
*Assistant Examiner*—D. B. Springer
*Attorney, Agent, or Firm*—Theresa Y. Cheng; Mario A. Monaco

[57] ABSTRACT

New 5-(2,3-dihydro-1H-pyrrolizin-5-oyl)-, 5-(2,3-dihydro-1H-pyrrolo[2,1-b]thiazol-5-oyl)-, 5-(2,3-dihydro-1H-pyrrolo[2,1-b]imidazol-5-oyl)-, and 5-(2,3-dihydro-1H-pyrrolo[2,1-b]oxazol-5-oyl)-pyrrole-2-alkanoic acid derivatives have been prepared. They are found to be effective inhibitors of platelet aggregation and are analgesic and anti-inflammatory agents with low ulcerogenic side effects.

7 Claims, No Drawings

5-(2,3-DIHYDRO-1H-PYRROLIZIN-5-OYL)-2-ALKANOIC OR CARBOXYLIC ACIDS AND ANALOGS AS ANTI-INFLAMMATORY AND ANALGESIC AGENTS

BACKGROUND OF THE INVENTION

The present invention relates to novel substituted new 5-(2,3-dihydro-1H-pyrrolizin-5-oyl)-, 5-(2,3-dihydro-1H-pyrrolo[2,1-b]thiazol-5-oyl)-, 5-(2,3-dihydro-1H-pyrrolo[2,1-b]imidazol-5-oyl)-, and 5-(2,3-dihydro-1H-pyrrolo[2,1-b]oxazol-5-oyl)-pyrrole-2-alkanoic acid derivatives and their corresponding salts, esters, nitriles, amides and substituted amides. These compounds are found to exhibit analgesic/anti-inflammatory activities with low ulcerogenic irritation. For a chronic disease, for example, arthritis, it is crucial that the anti-inflammatory/analgesic agent be administered routinely and regularly at an effective dosage level without causing gastric irritation or ulcers. Accordingly, it is an object of the present invention
(1) to provide novel nonsteroidal antiinflammatory and analgesic agents of lower ulcerogenic side effect;
(2) to develop processes for the preparation of the novel compounds;
(3) to provide methods of application of the novel compounds in the treatment of inflammatory diseases; and
(4) to provide pharmaceutical compositions and formulations for the administration of these novel compounds.

DETAILED DESCRIPTION OF THE INVENTION

This invention relates to novel 5-(2,3-dihydro-1H-pyrrolizin-5-oyl)pyrrole-2-alkanoic acids and analogs of the structural formula:

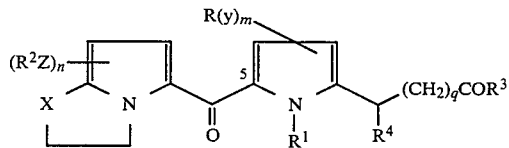

(I)

or a pharmaceutically acceptable salt, ester or amide thereof
wherein
R is
(a) hydrogen;
(b) loweralkyl especially $C_{1-6}$ linear or branched alkyl such as methyl, ethyl, propyl, isopropyl, t-butyl, pentyl, and hexyl;
(c) lowercycloalkyl especially $C_{3-6}$ cycloalkyl such as cyclopropyl, cyclobutyl, cyclopentyl and cyclohexyl;
(d) lower(cycloalkyl-alkyl) especially $C_{4-8}$(cycloalkyl-alkyl) such as cyclopropylmethyl, cyclopentylmethyl, cyclohexylmethyl and cyclohexylethyl;
(e) loweralkenyl especially $C_{2-8}$ alkenyl such as 2-propenyl, 2-methyl-2-butenyl and 3-ethyl-2-pentenyl;
(f) halo-loweralkyl especially halo $C_{1-6}$ alkyl such as chloromethyl, trifluoromethyl, 1-chloroethyl and 2,2-difluorobutyl;
(g) phenyl- or substituted phenyl-loweralkyl especially phenyl-$C_{1-3}$ alkyl such as benzyl, 4-chlorobenzyl, 2-fluorobenzyl, and phenylpropyl; or
(h) phenyl or substituted phenyl, e.g., p-methoxyphenyl or m-chloro-phenyl;
groups (a)-(h) above being unsubstituted or substituted by loweralkyl, loweralkoxy, halo, cyano, carboxy, sulfamoyl, sulfinamoyl, carbamoyl, sulfonyl, sulfinyl, azido, amino, substituted amino such as loweralkylamino or di(loweralkyl)amino, haloalkyl, carboxyalkyl, carbamoylalkyl, N-substituted carbamoylalkyl or a combination thereof;
m is 0 to 2;
$R^1$ is hydrogen, loweralkyl especially $C_{1-6}$ alkyl as previously defined, hydroxyalkyl, alkoxyalkyl, amino or alkylaminoalkyl, aryl, aralkyl, substituted aralkyl, alkanoyl or aroyl;
$R^2Z$ can be at any available ring positions and $R^2$ is R as previously defined;
q is 0 to 5;
n is 0 to 2;
$R^3$ is
(a) hydroxy;
(b) loweralkoxy especially $C_{1-6}$ alkoxy such as methoxy, ethoxy, isopropoxy, or n-butoxy;
(c) amino;
(d) loweralkylamino especially $C_{1-6}$ alkylamino such as cyclohexylamino, methylamino, isopropyl amino, n-butylamino or t-butylamino;
(e) diloweralkylamino especially di($C_{1-6}$ alkyl)amino such as diethylamino, or dimethylamino or ethylmethylamino;
(f) morpholinyl;
(g) bis(hydroxyloweralkyl)amino especially bis(hydroxy $C_{1-6}$ alkyl)amino such as bis(hydroxyethyl)amino;
(h) loweralkylcyclohexylamino especially $C_{1-6}$ alkylcyclohexylamino such as methylcyclohexylamino;
(i) glucosamino;
(j) lower(alkanoyloxyalkoxy), especially $C_{1-6}$(alkanoyloxyalkoxy) such as 2-(pivaloyloxy)ethoxy or 2-(acetoxy)ethoxy;
(k) aroyloxyloweralkoxy especially 2-(benzoyloxy)ethoxy;
(l) lower(alkoxycarbonyloxyalkoxy) especially $C_{1-6}$(alkoxycarbonyloxyalkoxy) such as 2-(ethoxycarbonyloxy)ethoxy;
(m) hydroxyalkyloxycarbonyloxy or polyhydroxyalkyloxycarbonyloxyalkoxy, e.g.

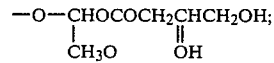

(n) aryloxycarbonyloxyloweralkoxy especially aryloxycarbonyl $C_{1-6}$ alkoxy such as 2-(phenoxycarbonyloxy)ethoxy;
(o) di(loweralkyl)aminoloweralkoxy especially di($C_{1-6}$alkyl)amino $C_{1-6}$ alkoxy such 2-dimethylaminoethoxy, 2-dimethylamino-n-propoxy, or 3-diethylamino-n-butoxy-;
(p) lower(alkanoylaminoalkoxy), especially $C_{1-6}$ (alkanoylaminoalkoxy) such as acetamidoethoxy;
(q) imidoloweralkoxy especially imido $C_{1-6}$ alkoxy such as 2-(1-succinimido)ethoxy;
(r) heterocyclyloxy or heterocycloalkylalkoxy, for example, phthalidyloxy, 2-pyridyloxy,

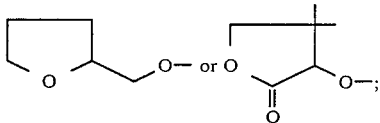

(s) hydroxyloweralkoxy especially hydroxy $C_{1-6}$ alkoxy such as hydroxypropoxy;

(t) loweralkoxyalkoxy especially $C_{1-6}$(alkoxyalkoxy) such as methoxyethoxy, ethoxyethoxy or methoxymethoxy;

(u) lower di(alkyl)aminoalkylamino such as $(C_2H_5)_2NCH_2CH_2NH$;

(v) N-pyrrolidinylloweralkoxy especially N-pyrrolidinyl $C_{1-6}$ alkoxy such as N-pyrrolidinylethoxy or N-pyrrolidinyl methoxy and N-methyl-2-pyrrolidinylmethoxy;

(w) N-piperidinylloweralkoxy especially N-piperidinyl $C_{1-6}$ alkoxy such as N-piperidinylethoxy;

(x) N-morpholinylloweralkoxy especially N-morpholinyl $C_{1-6}$alkoxy such as N-morpholinylethoxy; or (y) 4-methyl-1-piperazinylloweralkoxy especially 4-methyl-1-piperazinyl-$C_{1-6}$ alkoxy such as 4-methyl-1-piperazinylethoxy;

X is —O—, —S—, —SO—, —$SO_2$—, —$NR^5$— or —$CHR^5$—;

Y is —O—, —S—, —SO—, —$SO_2$—, $CHR^5$— or hydrogen providing that when Y is hydrogen, R does not exist;

Z is —O—, —S—, —SO—, —$SO_2$—, —$NR^5$—, —$CHR^5$— or halo especially fluoro, chloro or bromo providing that when Z is halo, $R^2$ does not exist;

$R^4$ is hydrogen, loweralkyl especially $C_{1-6}$ alkyl, loweralkoxy, halo, loweralkenyl especially $C_{1-6}$ alkenyl such as allyl, methylene, oxo, hydroxy, amino, alkylamino or di(alkyl)amino;

$R^5$ is hydrogen or $C_{1-6}$ alkyl as previously defined.

The preferred embodiment of this invention comprises compounds of formula (I) wherein R is (a) hydrogen or $C_{1-6}$ alkyl as previously defined;

(b) $C_{2-4}$ alkenyl such as 2-propenyl or propenylmethyl;

(c) halo$C_{1-6}$ alkyl as previously defined; or (d) phenyl-$C_{1-3}$ alkyl such as benzyl;

m is 0 or 1;

$R^1$ is hydrogen or $C_{1-6}$ alkyl;

$R^2Z$ is as defined above;

q is 0 to 2;

n is 0 or 1;

$R^3$ is hydroxy, $C_{1-6}$ alkoxy, or lower(alkanoylaminoalkoxy), especially $C_{1-6}$ alkanoylaminoalkoxy such as acetamidoethoxy;

X is —S—, —SO—, or —$CHR^5$;

Y is —O—, —S—, —$CH_2$—, or H when R is absent;

Z is —S—, —$CH_2$—, or halo when $R^2$ is absent;

$R^4$ is hydrogen or $C_{1-6}$ alkyl; and $R^5$ is methyl or hydrogen.

The most preferred embodiment of this invention comprises compounds of structural formula (I) wherein R is absent or $C_{1-3}$ alkyl especially methyl;

m is 0 or 1;

$R^1$ is hydrogen or $C_{1-6}$ alkyl;

$R^2Z$ is as defined previously;

q is 0 or 1;

n is 0 or 1;

$R^3$ is hydroxy, $C_{1-6}$ alkoxy or acetamidoethoxy;

X is —S—, —SO—, or —$CHR^5$—;

Y is —O—, —$CH_2$—, or H with the proviso that when Y is H, R is absent;

Z is —S—, —$CH_2$—, or halo with the proviso that when Z is halo, $R^2$ is absent;

$R^4$ is hydrogen or $C_{1-6}$ alkyl; and $R_5$ is methyl or hydrogen.

Representative compounds of this invention include:

(a) 5-(2,3-dihydro-1H-pyrrolizin-5-oyl)-1,4-dimethylpyrrole-2-acetic acid; and (b) ethyl 5-(2,3-dihydro-1H-pyrrolizin-5-oyl)-1,4-dimethylpyrrole-2-acetate.

The novel compounds of the present invention can be prepared by the following schemes (A) and (B):

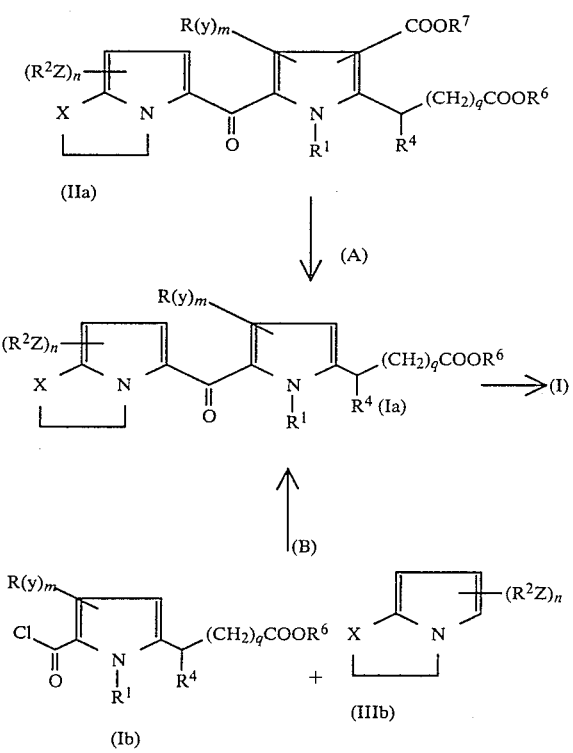

Wherein R, $R^1$, $R^2$, $R^4$, X, Y, Z, n, m and q are as previously defined; $R^6$ is hydrogen, loweralkyl especially $C_{1-6}$ alkyl such as methyl, ethyl, isopropyl, t-butyl, pentyl, or cyclohexyl, and $R^7$ is hydrogen, t-butyl, n-butyl, benzhydryl or other protecting groups which can be removed under mild conditions.

I. According to scheme (A) above, IIa is decarboxylated under neutral, acidic or basic conditions or by itself (neat). When the decarboxylation is conducted under basic conditions, the precursor of formula IIa is usually heated with a base (Table I) in an appropriate solvent at about 50°–250° C. preferably about 90°–150° C. for about 0.5–48 hours or until the decarboxylation is substantially complete.

The most commonly utilized solvents comprise (1) water;

(2) $C_{1-5}$ alkanol especially methanol, ethanol, isopropanol and t-butyl alcohol;

(3) lower ketone, e.g., acetone and methylethylketone;

(4) lower ether including diethylether, 1,2-dimethoxyethane, tetrahydrofuran (THF), dioxane and diglyme;
(5) a mixture of at least two of the solvents described in (1) to (4).

TABLE I
Organic Bases Used in Decarboxylation

Tri-(loweralkyl)amine, e.g., triethylamine
pyrrolidine
pyridine
collidine
ethanolamine
quinoline etc.

When acidic decarboxylation is applied, IIa is refluxed in trifluoroacetic acid, for example, to give Ia which is then subject to various known modifications such as hydrolysis (when $R^4$ is not H), aminolysis, ester exchange etc. to afford (I). Other acids may also be used, for example, those listed below in Table II.

TABLE II

Acids Used in the Decarboxylation (1) An acid of the structural formula:

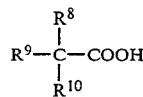

wherein $R^8$ and $R^{10}$ independently are hydrogen or halo such as iodo, bromo, chloro or fluoro preferably chloro or fluoro; and $R^9$ is H, $C_{1-6}$ alkyl, halo especially chloro or fluoro, or halo-$C_{1-6}$ alkyl such as trifluoromethyl, trichloromethyl, 1,1-difluoroethyl, or 1-chloro-1-fluoropropyl or the like.
(2) Preferred Acids:
Acetic acid
Chloroacetic acid
Chlorodifluoroacetic acid
Dichloroacetic acid
Difluoroacetic acid
Trifluoroacetic acid
Trichloroacetic acid
Pentafluoropropanoic acid The acidic decarboxylation may be conducted in an acid or in an inert solvent containing the acid. The solvents which are often used are illustrated below in Table III.

TABLE III
Solvents for the Acidic Decarboxylation

Toluene
Benzene
Xylene
Tetrahydrofuran
1,2-Dimethoxyethane
Dioxane
Methylene chloride
Acetic Acid The decarboxylation temperatures may vary with the acids or solvents being used. Usually the temperatures range from about 30° to about 120° C. Under the optimum conditions, i.e., in refluxing trifluoroacetic acid with or without solvent, the temperature ranges from about 35° to 75° C.

Generally, the decarboxylation is substantially complete after heating at an appropriate temperature for about 1 to about 20 hours or under more favorable conditions, about 0.5 hours to about 5 hours.

It should be noted that IIa can be decarboxylated directly to I when $R^6$ and $R^7$ independently are hydrogen, t-butyl, benzhydryl or other acid-removable protecting groups.

II. Alternatively, according to scheme (B) reaction between (Ib) and (IIIb) forms Ia which upon optional and appropriate modification (e.g., hydrolysis, esterification, or aminolysis) affords I. These modifications e.g., hydrolysis procedures are described in the copending application Ser. No. 373,692, filed May 3, 1982 and are incorporated herein by reference.

The precursors having formula (Ia) or (IIa) are readily prepared from condensation between a pyrrole derivative (IVa) and a substituted 2,3-dihydro-1H-pyrrolizinyl derivative (IIIb) as shown below in scheme (a):

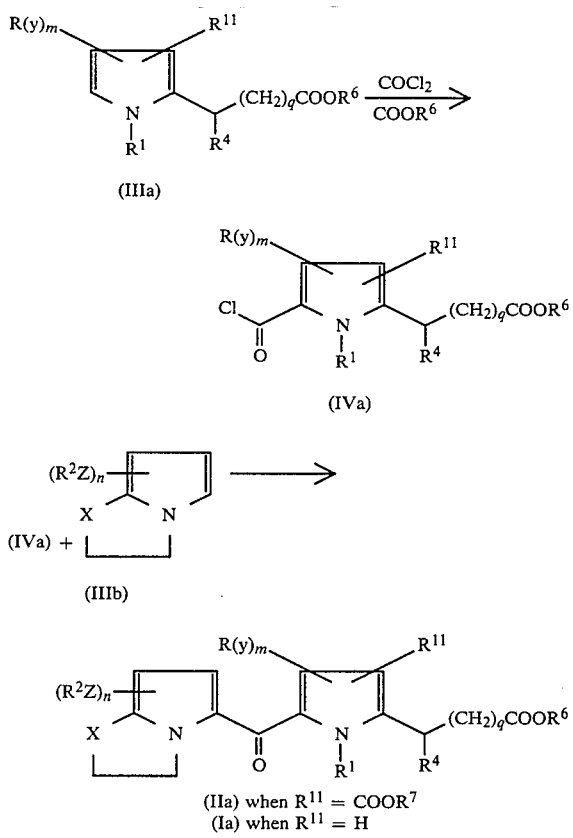

wherein R, $R^1$, $R^4$, $R^6$, $R^7$, m, q, n, X, Y and Z are as previously defined; and $R^{11}$ is H or —$COOR^7$.

Alternatively (Ia) and (IIa) may be obtained via route (b) as follows:

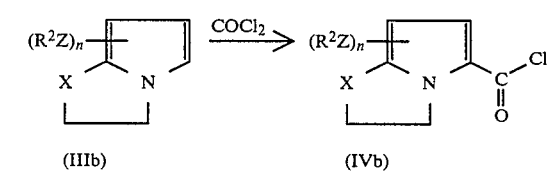

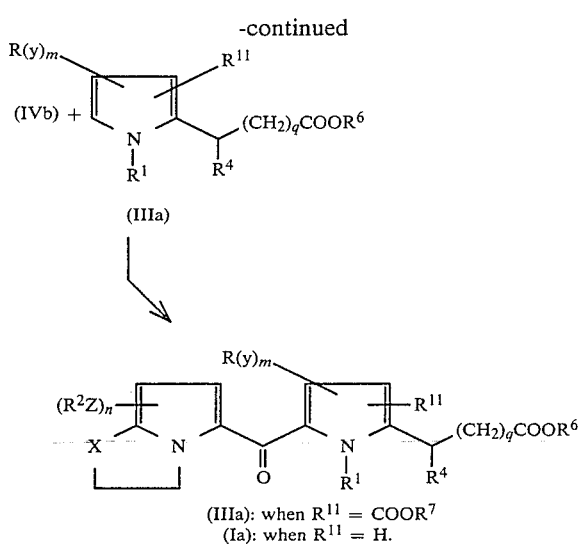

(IIIa): when $R^{11}$ = $COOR^7$
(Ia): when $R^{11}$ = H.

Other starting materials are known or readily preparable by procedures described in copending applications Ser. No. 387,079, filed June 10, 1982, Ser. No. 443,339, filed Oct. 8, 1982 and U.S. Pat. No. 4,097,579. These disclosures are herein incorporated by reference.

The pharmaceutically acceptable satls of the acids of the Formula I are readily prepared by conventional procedures well-known in the art. For example, an acid of Formula I is treated with an appropriate amount of a base, such as an alkali or alkaline earth metal hydroxide, e.g. sodium hydroxide, potassium hydroxide, calcium hydroxide, or an organic base such as an amine, e.g., triethylamine, lysine, dibenzylethylenediamine, piperidine, pyrrolidine, benzylamine and the like.

The pharmaceutically acceptable esters of the acids of structural formula (I) are prepared by conventional methods. For example, (1) A compound of Formula (I) is treated with a lower alkanol or phenol in the presence of an acid such as sulfuric acid, hydrochloric acid, boron trifluoride or the like.

(2) A compound of Formula (I) is converted to an acid halide such as acid chloride or bromide via treatment with a halogenating agent such as thionyl chloride or phosphorus pentachloride, followed by reaction with an alcohol or a phenol.

(3) A compound of formula (I) is reacted with an alcohol in the presence of a condensing agent such as N,N'-dicyclohexylcarbodiimide (DCC) or the like. Other well-known methods such as those included in the "Compendium of Organic Synthetic Methods," I. T. Harrison et al., Wiley-Interscience, p. 272 (1971), may also be used.

Similarly, the pharmaceutically acceptable amides of the acids of Formula (I) are readily prepared by conventional methods. For example, the esters or halides of the acids of Formula (I) can be treated with ammonia or substituted amines such as ethylamine, benzylamine or other amines to afford the corresponding amides. Other methods involving treatment of the acids with an amine in the presence of a catalyst such as DCC may also be used.

The novel compounds of this invention are anti-inflammatory and analgesic agents of value in the treatment of a wide variety of conditions where one or more of the symptoms of pain or inflammation are manifested, e.g., rheumatoid arthritis, osteoarthritis, gout, infectious arthritis, rheumatic fever and pain symptoms associated with other diseases.

For treatment of inflammation, fever or pain, the compounds of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active compounds of this invention may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, maize starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active inngredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl- or n-propyl-p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional escipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

Dosage levels of the order to 0.2 mg to 140 mg per kilogram of body weight per day are useful in the treatment of the above-indicated conditions (10 mg to 7 gms. per patient per day). For example, inflammation is effectively treated and anti-pyretic and analgesic activity manifested by the administration from about 0.5 to 50 mg of the compound per kilogram of body weight per day (25 mg to 3.5 gms per patient per day). Advantageously, from about 2 mg to about 20 mg per kilogram of body weight per daily dosage produces highly effective results (50 mg to 1 gm per patient per day).

The amount of active ingredients that may be combined with the carrier materials to produce a single dosage form will vary depending upon the host treated and the particular mode of administration. For example, a formulation intended for the oral administration of humans may contain from 5 mg to 5 gm of active agent compounded with an appropriate and convenient amount of carrier material which may vary from about 5 to about 95 percent of the total composition. Dosage unit forms will generally contain between from about 25 mg to about 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples are provided for illustrating but not limiting the scope of the present invention.

EXAMPLE 1

1,4-Dimethyl-5-(2,3-dihydro-1H-pyrrolizin-5-oyl)-pyrrole-2-acetic acid

Step A: Preparation of Methyl 1,4-dimethyl-5-(2,3-dihydro-1H-pyrrolizin-5-oyl)-pyrrole-2-acetate To a stirred, ice-cooled mixture of 2,3-dihydro-1H-pyrrolizine (0.40 g, 0.0037 m), methyl 5-(chlorocarbonyl)-1,4-dimethylpyrrole-2-acetate (1.1 g, 0.0037 m), and methylene chloride (10 ml) was added dropwise over 3 minutes stannic chloride (0.86 ml, 0.0075 m), and the resulting mixture allowed to stir cold for ca. 30 minutes. The mixture was partitioned between ether and water, and the ether layer washed and dried. It was concentrated in vacuo to a yellow residue which was then eluted on a silica gel chromatograph column with 30% ethyl acetate/hexane to yield 0.35 g of methyl 1,4-dimethyl-5-(2,3-dihydro-1H-pyrrolizin-5-oyl)pyrrole-2-acetate.

Step B: Preparation of 1,4-Dimethyl-5-(2,3-dihydro-1H-pyrrolizin-5-oyl)-pyrrole-2-acetic acid Hydrolysis of the ester from Step A above in the usual manner yields 1,4-dimethyl-5-(2,3-dihydro-1H-pyrrolizin-5-oyl)-pyrrole-2-acetic acid, m.p. 132°–134° C.

Following substantially the same procedures as described above, the following compounds are also prepared from the corresponding starting materials listed below:

| Starting Materials | Compound |
|---|---|
| 2,3-dihydro-1-methyl-1H—pyrrolidone | ethyl 5-(2,3-dihydro-1-methyl-1H—pyrrolidone-5-oyl)-1,4-dimethylpyrrole-2-acetate and the corresponding acid. |
| 2,3-dihydropyrrolo[2,1-b]-thiazole | ethyl 5-(2,3-dihydro-pyrrolo[2,1-b]thiazol-5-oyl)1,4-dimethylpyrrole-2-acetate and the corresponding acid. |

What is claimed is:

1. A compound of formula

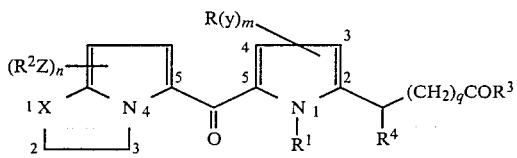

or a pharmaceutically acceptable salt thereof
wherein:
R is
 (a) H or $C_{1-6}$ alkyl;
 (b) $C_{2-4}$ alkenyl;
 (c) halo$C_{1-6}$ alkyl; or
 (d) phenyl-$C_{1-3}$ alkyl;
m is 0 or 1;
$R^1$ is H or $C_{1-6}$ alkyl;
$R^2Z$ is $R^2Z$ can be at any available positions and $R^2$ is R
q is 0;
n is 0 or 1;
$R^3$ is hydroxy, $C_{1-6}$ alkoxy or $C_{1-6}$ (alkanoylaminoalkoxy);
X is —$CHR^5$—;
Y is —O—, —S—, $CH_2$— or H with the proviso that when Y is H, R is absent;
Z is —S—, —$CH_2$— or halo with the proviso that when Z is halo, $R^2$ is absent;
$R^4$ is hydrogen or $C_{1-6}$alkyl; and
$R^5$ is methyl or hydrogen.

2. The compound of claim 1 wherein
R is absent or $C_{1-3}$ alkyl;
m is 0 or 1;
$R^1$ is H or $C_{1-6}$ alkyl;
$R^2Z$ is as defined previously;
q is 0;
n is 0 or 1;
$R^3$ is hydroxy, $C_{1-6}$ alkoxy or acetamidoethoxy;
X is —$CH_2$—, or

Y is —O—, $CH_2$— or H with the proviso that when Y is H, R is absent; and
Z is —S—, —$CH_2$—, or halo with the proviso that when Z is halo, $R^2$ is absent;
$R^4$ is hydrogen or $C_{1-6}$alkyl; and
$R^5$ is hydrogen or methyl.

3. The compound of claim 1 which is
(a) 5-(2,3-dihydro-1H-pyrrolizin-5-oyl)-1,4-dimethylpyrrole-2-acetic acid; or
(b) ethyl 5-(2,3-dihydro-1H-pyrrolizin-5-oyl)-1,4-dimethylpyrrole-2-acetate.

4. A pharmaceutical composition for treating inflammatory conditions in Mammalian species comprising a non-toxic pharmaceutical carrier and an effective amount of a compound of structural formula:

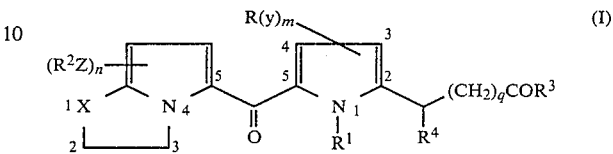

or a pharmaceutically acceptable salt thereof
wherein:
R is
 (a) H or $C_{1-6}$ alkyl;
 (b) $C_{2-4}$ alkenyl;
 (c) halo$C_{1-6}$ alkyl; or
 (d) phenyl-$C_{1-3}$ alkyl;
m is 0 or 1;
$R^1$ is H or $C_{1-6}$ alkyl;
$R^2Z$ is $R^2Z$ can be at any available positions and $R^2$ is R
q is 0;
n is 0 or 1;
$R^3$ is hydroxy, $C_{1-6}$ alkoxy or $C_{1-6}$ (alkanoylaminoalkoxy);
X is —$CHR^5$—;
Y is —O—, —S—, $CH_2$— or H with the proviso that when Y is H, R is absent;
Z is —S—, —$CH_2$— or halo with the proviso that when Z is halo, $R^2$ is absent;
$R^4$ is hydrogen or $C_{1-6}$alkyl; and
$R^5$ is methyl or hydrogen.

5. The pharmaceutical composition of claim 4 wherein
R is absent or $C_{1-3}$ alkyl;
m is 0 or 1;
$R^1$ is H or $C_{1-6}$ alkyl;
$R^2Z$ is as defined previously;
q is 0;
n is 0 or 1;
$R^3$ is hydroxy, $C_{1-6}$ alkoxy or acetamidoethoxy;
X is —$CH_2$—, or

Y is —O—, $CH_2$— or H with the proviso that when Y is H, R is absent; and
Z is —S—, —$CH_2$—, or halo with the proviso that when Z is halo, $R^2$ is absent;
$R^4$ is hydrogen or $C_{1-6}$alkyl; and
$R^5$ is hydrogen or methyl.

6. A method of treating inflammatory conditions which comprises the administration to a mammalian species in need of such treatment an effective amount of a compound of formula

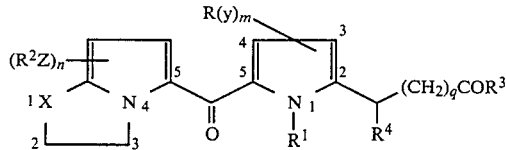

or a pharmaceutically acceptable salt thereof
wherein:
R is
(a) H or $C_{1-6}$ alkyl;
(b) $C_{2-4}$ alkenyl;
(c) halo$C_{1-6}$ alkyl; or
(d) phenyl-$C_{1-3}$ alkyl;
m is 0 or 1;
$R^1$ is H or $C_{1-6}$ alkyl;
$R^2Z$ is $R^2Z$ can be at any available positions and $R^2$ is R
q is 0;
n is 0 or 1;
$R^3$ is hydroxy, $C_{1-6}$ alkoxy or $C_{1-6}$ (alkanoylaminoalkoxy);
X is —$CHR^5$—;

Y is —O—, —S—, $CH_2$— or H with the proviso that when Y is H, R is absent;
Z is —S—, —$CH_2$— or halo with the proviso that when Z is halo, $R^2$ is absent;
$R^4$ is hydrogen or $C_{1-6}$alkyl; and
$R^5$ is methyl or hydrogen.
7. The method of claim 6 wherein
R is absent or $C_{1-3}$ alkyl;
m is 0 or 1;
$R^1$ is H or $C_{1-6}$ alkyl;
$R^2Z$ is as defined previously;
q is 0;
n is 0 or 1;
$R^3$ is hydroxy, $C_{1-6}$ alkoxy or acetamidoethoxy;
X is —$CH_2$—, or

Y is —O—, $CH_2$— or H with the proviso that when Y is H, R is absent; and
Z is —S—, —$CH_2$—, or halo with the proviso that when Z is halo, $R^2$ is absent;
$R^4$ is hydrogen or $C_{1-6}$alkyl; and
$R^5$ is hydrogen or methyl.

* * * * *